(12) United States Patent
Sakashita

(10) Patent No.: US 10,441,720 B2
(45) Date of Patent: Oct. 15, 2019

(54) MEDICAL SYRINGE

(71) Applicant: SUMITOMO RUBBER INDUSTRIES, LTD., Kobe-shi, Hyogo (JP)

(72) Inventor: Yuki Sakashita, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 106 days.

(21) Appl. No.: 15/827,381

(22) Filed: Nov. 30, 2017

(65) Prior Publication Data

US 2018/0177951 A1 Jun. 28, 2018

(30) Foreign Application Priority Data

Dec. 28, 2016 (JP) ................. 2016-255269

(51) Int. Cl.
*A61M 5/315* (2006.01)
*B29L 31/00* (2006.01)
*B29K 27/18* (2006.01)

(52) U.S. Cl.
CPC . *A61M 5/31513* (2013.01); *A61M 2205/0222* (2013.01); *A61M 2205/0238* (2013.01);
(Continued)

(58) Field of Classification Search
CPC .............. A61M 5/31513; A61M 5/315; A61M 5/31511; A61M 5/31; A61M 39/0208;
(Continued)

(56) References Cited

U.S. PATENT DOCUMENTS 6,090,081 A 7/2000 Sudo et al.
6,575,938 B2 * 6/2003 Sayama ............ A61M 5/31513
604/181

(Continued)

FOREIGN PATENT DOCUMENTS

JP 10-314305 A 12/1998
JP 2004-525011 A 8/2004
(Continued)

*Primary Examiner* — Manuel A Mendez
(74) *Attorney, Agent, or Firm* — Birch, Stewart, Kolasch & Birch, LLP

(57) ABSTRACT

Medical syringe having a gasket excellent in sealability and slidability. The syringe includes a hollow cylindrical syringe barrel (11) and a gasket (13) fitted in syringe barrel (11). Gasket (13) includes a main body of an elastic material laminated with an inert resin film and has a circumferential surface portion (17) substantially maintained in contact with an inner surface (16) of syringe barrel (11). Gasket 13 also has an annular projection (22), provided on circumferential surface portion (17), extending circumferentially of circumferential surface portion (17). Projection (22) has a contact surface portion maintained in contact with inner surface (16) of syringe barrel (11) and having a width of 30 μm to 40 μm. Circumferential surface portion (17) has non-contact surface portions located out of contact with inner surface (16) of syringe barrel (11) on widthwise opposite sides of projection (22) and having a width of at least 30 μm.

4 Claims, 4 Drawing Sheets

(52) U.S. Cl.
CPC ...... *A61M 2207/00* (2013.01); *B29K 2027/18* (2013.01); *B29L 2031/7544* (2013.01)

(58) Field of Classification Search
CPC ....... F16J 15/02; A61L 31/048; B65D 51/002; Y02E 60/521; Y02E 60/12; Y02E 60/122; Y02P 20/544; Y02P 70/56; B32B 27/32; B32B 27/08; H01G 9/155; H01M 2/1686
USPC ....................................................... 604/222
See application file for complete search history.

(56) References Cited

U.S. PATENT DOCUMENTS

| | | |
|---|---|---|
| 2004/0099994 A1 | 5/2004 | Brinkhues |
| 2006/0178643 A1 | 8/2006 | Sudo et al. |

FOREIGN PATENT DOCUMENTS

| | | |
|---|---|---|
| JP | 2006-181027 A | 7/2006 |
| JP | 4908617 B2 | 4/2012 |

\* cited by examiner

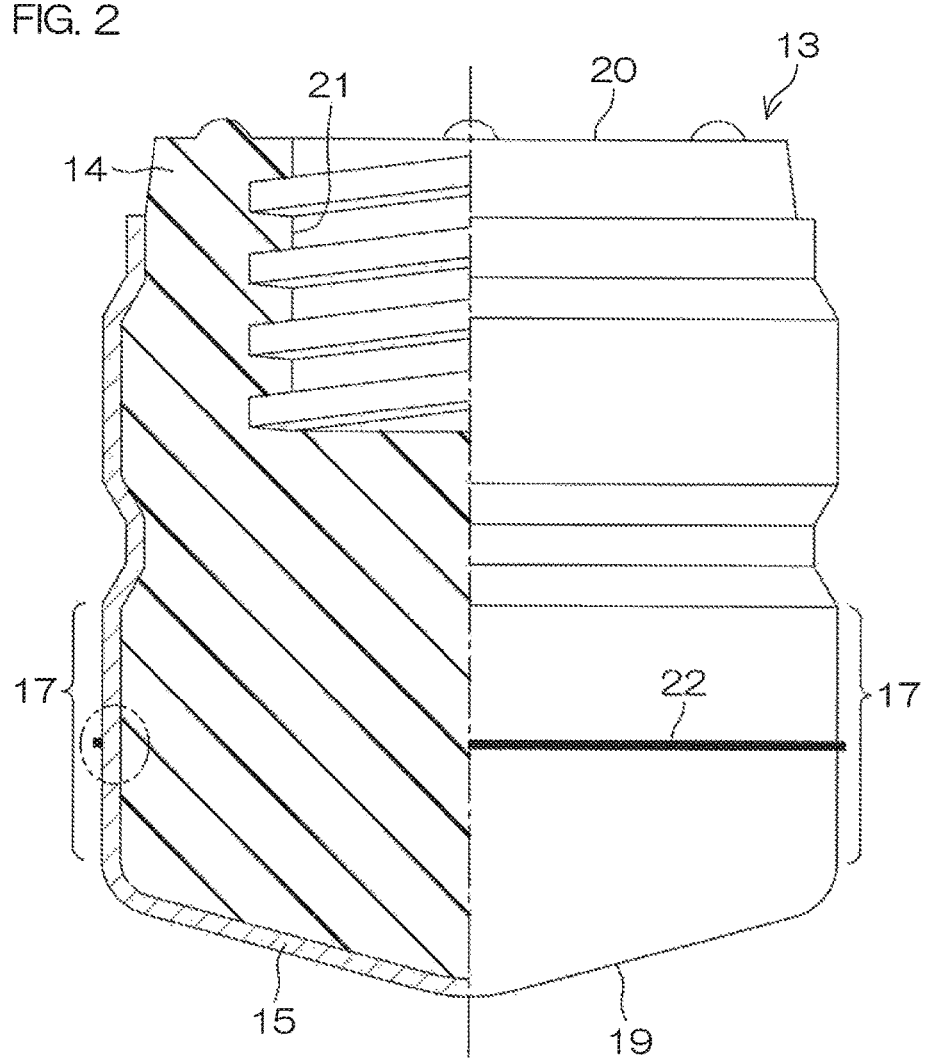

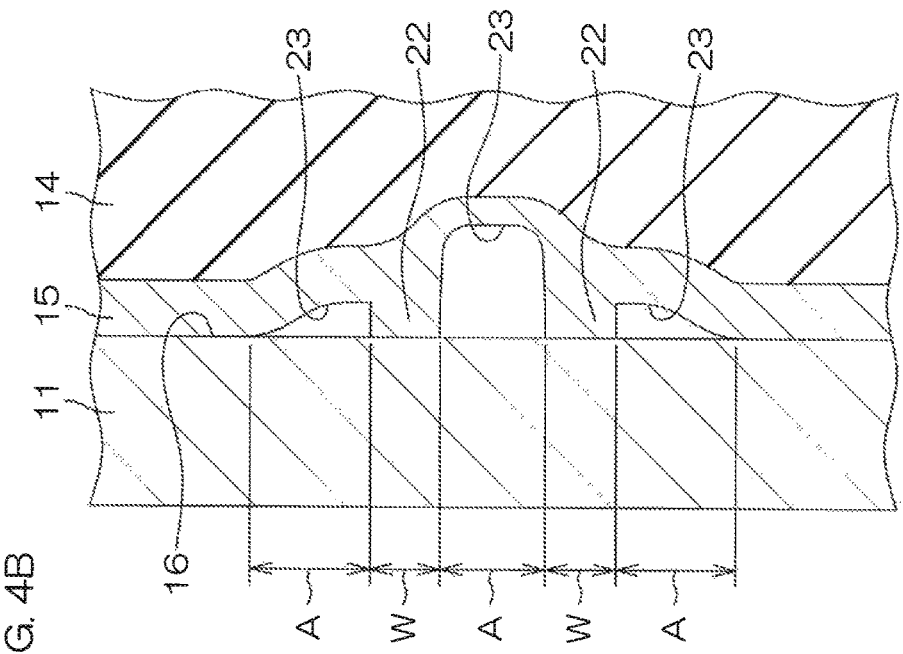
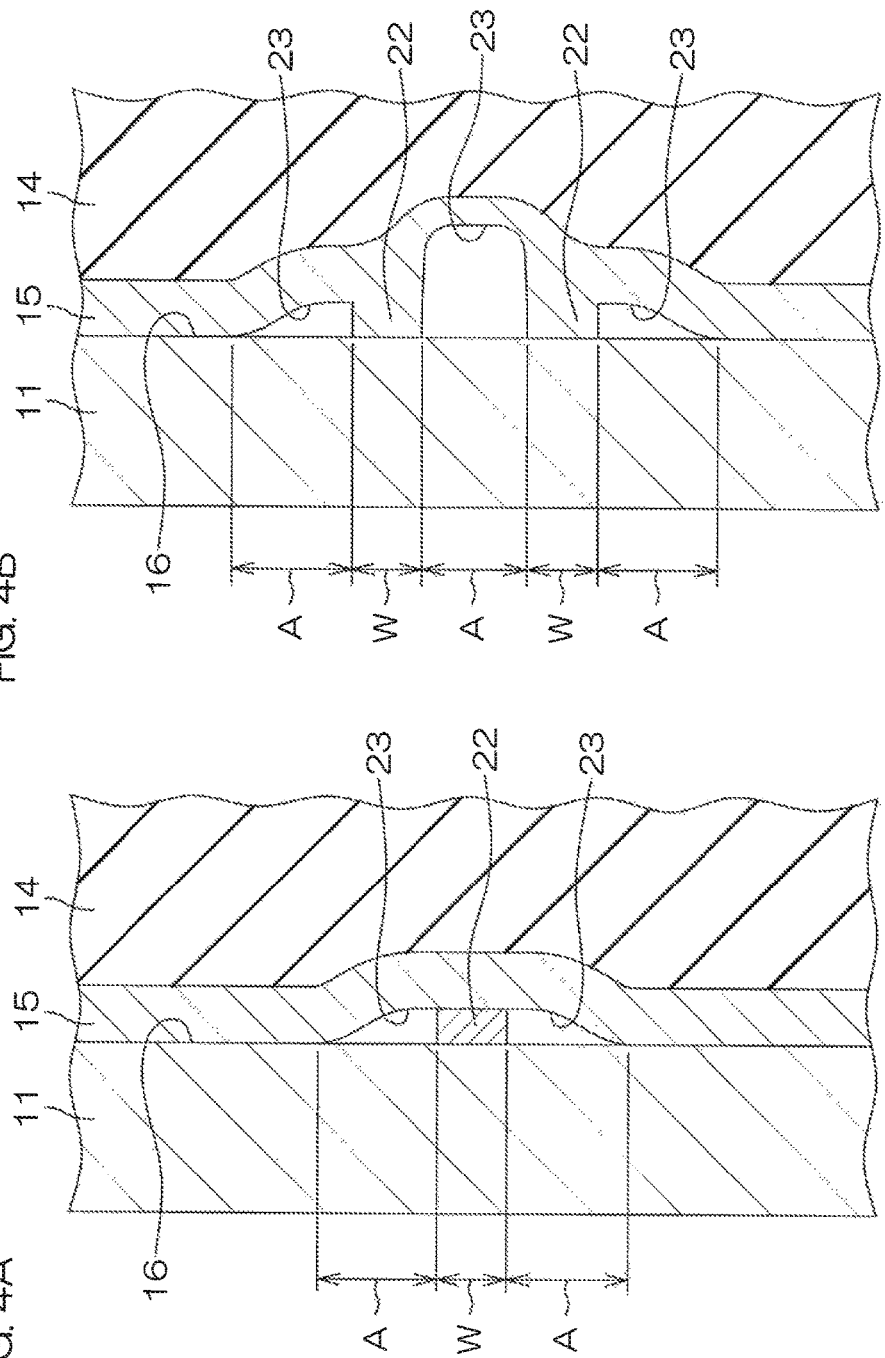
FIG. 4A
FIG. 4B

MEDICAL SYRINGE

TECHNICAL FIELD

The present invention relates to a medical syringe, particularly to a gasket to be used for the medical syringe.

BACKGROUND ART

Syringes prefilled with a liquid drug (generally referred to as "prefilled syringes") are used as medical syringes. The prefilled syringes are advantageous because of their handling ease without the need for transferring the liquid drug into the syringes. Further, transfer of a wrong liquid drug into the syringe is advantageously prevented. Therefore, the prefilled syringes are increasingly used in recent years.

Unlike conventional syringes into which a liquid drug sucked up from a vial or other container is transferred immediately before use, the prefilled syringes are each required to serve as a container which is kept in contact with the liquid drug for a long period of time.

Such a syringe typically includes a syringe barrel, and a gasket inserted in the syringe barrel.

The gasket to be inserted in the syringe is generally made of a crosslinked rubber. It is known that the crosslinked rubber contains various crosslinking components, and these components and their thermally decomposed products are liable to migrate into the liquid drug when the liquid drug is kept in contact with the gasket. It is also known that these migrating components adversely influence the efficacy and the stability of some liquid drug.

Further, the gasket is required to be smoothly slidable in the syringe barrel when the syringe is used.

In general, the gasket made of the crosslinked rubber is poorer in slidability. To cope with this, it is a general practice to apply silicone oil to an inner surface of the syringe barrel. However, it is also known that the silicone oil adversely influences the efficacy and the stability of some liquid drugs.

From this viewpoint, a product known as a "laminated gasket," including a rubber gasket body having a surface laminated with a highly slidable film, is often used for the medical syringe. Since the surface of the rubber gasket body of the laminated gasket is covered with the highly slidable film, it is possible to ensure the slidability even without the use of the silicone oil while preventing the components of the crosslinked rubber from migrating into the liquid drugs.

CITATION LIST

Patent Document

Patent Document 1: JP-HEI10 (1998)-314305A
Patent Document 2: JP-2006-181027A
Patent Document 3: JP-2004-525011A

SUMMARY OF THE INVENTION

Problem to be Solved by the Invention

In the laminated gasket, however, the film to be used for the lamination of the surface is not elastic and, therefore, is liable to impair the elasticity of the inside crosslinked rubber. The elasticity of the gasket is an essential requirement for reliable sealing of the liquid drug contained in the syringe barrel. If the gasket has insufficient elasticity, the liquid drug contained in the syringe barrel is liable to leak out of the syringe barrel. Further, the slidability of the gasket inserted in the syringe barrel also requires improvement.

To cope with this problem, Patent Document 1 proposes a gasket laminated with a tetrafluoroethylene (PTFE) film by a casting method. However, the aforementioned production method, which is a unique production method, is not practical, and is liable to reduce the liquid sealability of the gasket because minute irregularities on a mold surface are transferred onto the surface of the lamination film.

Patent Document 2 proposes a laminated gasket which has a plurality of ring projections provided on a sliding surface thereof and having different outer shapes. However, the ring projections are problematic in slidability because of their greater widths.

Patent Document 3 proposes a production method for producing a laminated gasket including an inert resin film provided on a gasket body as extending to a middle of a first annular seal portion thereof to be brought into contact with an inner wall of the syringe barrel. With this production method, a smaller size gasket can be produced. However, it is difficult to produce a greater size gasket because of difficulty in stamping.

The inventors of the present invention conducted studies to cope with these problems and, as a result, found that the problems can be solved by forming an annular projection on a lamination film on a circumferential surface portion of a gasket so that non-contact surface portions are provided on opposite sides of the annular projection to be kept out of contact with the inner surface of the syringe barrel.

In view of the foregoing, it is an object of the present invention to provide a medical syringe which is excellent in the sealability of a gasket thereof and substantially free from increase in the sliding resistance of the gasket.

Solution to Problems

An inventive medical syringe is defined in paragraphs [0016]-[0018] below.

According to a first inventive aspect, there is provided a syringe, which includes a hollow cylindrical syringe barrel, and a gasket fitted in the syringe barrel, wherein the gasket includes a main body made of an elastic material, and an inert resin film provided on a surface of the main body, wherein the gasket has a circumferential surface portion substantially kept in contact with an inner surface of the syringe barrel, and an annular projection provided on a surface of the circumferential surface portion as extending circumferentially of the circumferential surface portion, wherein the projection has a contact surface portion kept in contact with the inner surface of the syringe barrel and having a width of not less than 30 μm and not greater than 40 μm, wherein the circumferential surface portion has non-contact surface portions located out of contact with the inner surface of the syringe barrel on widthwise opposite sides of the projection and having a width of not less than 30 μm.

According to a second inventive aspect, the inert resin film comprises at least one of a polytetrafluoroethylene, an ethylene-tetrafluoroethylene copolymer and an ultrahigh-molecular-weight polyethylene, and a mixture of any of these polymers.

According to a third inventive aspect, the syringe is a prefilled syringe prefilled with a liquid drug.

Effects of the Invention

According to the present invention, a medical syringe, particularly a prefilled syringe, can be provided, which is excellent in the slidability and the sealability of the gasket, and free from adverse influence on the efficacy and the stability of a liquid drug even if the syringe is kept in contact with the liquid drug for a long period of time.

BRIEF DESCRIPTION OF THE DRAWINGS

FIG. 2 is a diagram of a laminated gasket according to the embodiment of the present invention with a half of the gasket illustrated in cross-section.

FIGS. 4A and 4B are enlarged sectional views each showing a contact portion between a circumferential surface portion of the gasket and an inner surface of a syringe barrel of the medical syringe according to the embodiment of the present invention.

EMBODIMENTS OF THE INVENTION

With reference to the attached drawings, one embodiment of the present invention will hereinafter be described specifically.

Figure 1:
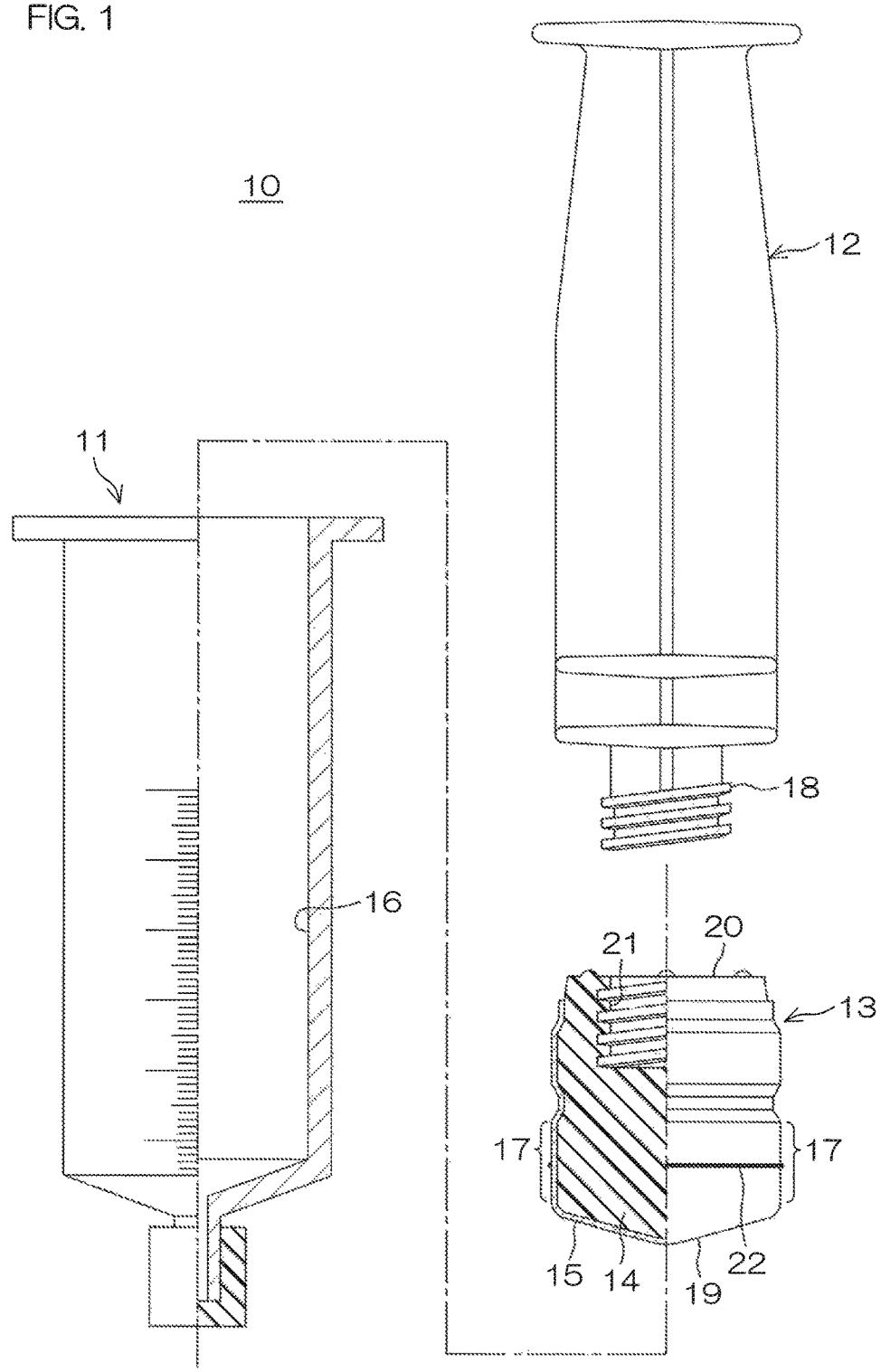
FIG. 1 is an exploded diagram illustrating a medical syringe according to an embodiment of the present invention.

FIG. 1 is an exploded diagram illustrating a medical syringe, i.e., a so-called prefilled syringe, according to the embodiment of the present invention. In FIG. 1, a half of a syringe barrel 11 and a half of a gasket 13 are illustrated in cross-section.

Referring to FIG. 1, the prefilled syringe 10 includes a hollow cylindrical syringe barrel 11, a plunger 12 combined with the syringe barrel 11 and reciprocally movable in the syringe barrel 11, and a gasket 13 attached to a distal end of the plunger 12.

The gasket 13 is a so-called laminated gasket, which includes a main body 14 made of an elastic material (a rubber or an elastomer) and an inert resin film 15 provided on a surface of the main body 14. The gasket 13 has a circumferential surface portion 17 to be kept in gas-tight and liquid-tight contact with an inner surface 16 of the syringe barrel 11. An annular projection 22 is provided on the circumferential surface portion 17 as extending circumferentially of the circumferential surface portion 17.

The plunger 12 includes a resin plate piece, for example, having a shape as seen in cross-section, and a head 18 provided at a distal end of the resin plate piece and fitted with the gasket 13. The head 18 is an integral part of the plunger 12 made of a resin and shaped in a male screw.

The gasket 13 has a generally cylindrical shape having a short axis. The gasket 13 has a distal end face 19, for example, having a conical center portion projecting at an obtuse angle, and a rear end face 20 axially recessed into an engagement recess 21 shaped in a female screw. The head 18 of the plunger 12 is screwed into the engagement recess 21 of the gasket 13, whereby the gasket 13 is attached to the distal end of the plunger 12.

Where a liquid drug to be contained in the syringe barrel 11 is not adversely influenced by generally usable silicone oil or curable silicone, the silicone oil or the curable silicone may be applied on the inner surface 16 of the syringe barrel 11 or on a surface of the gasket 13 to ensure higher slidability of the gasket 13 with respect to the syringe barrel 11.

Figure 3B:
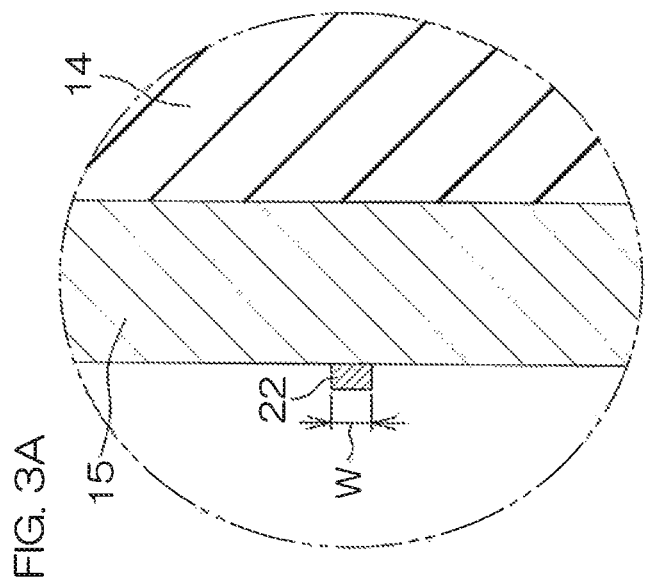
FIGS. 3A and 3B are enlarged views each showing a major portion of the laminated gasket according to the embodiment of the present invention.
Figure 3A:
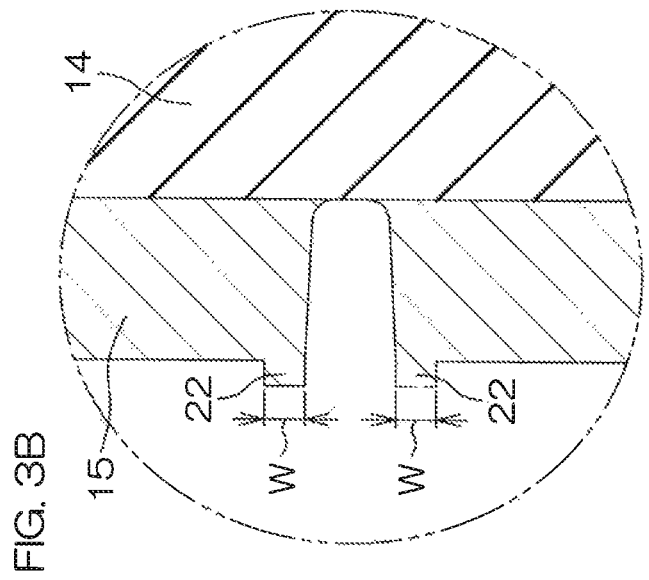

FIG. 2 is a diagram showing only the gasket 13 of FIG. 1 on an enlarged scale with a half of the gasket 13 illustrated in cross-section. FIGS. 3A and 3B are enlarged views each showing a major portion of the gasket 13. FIG. 3A shows a case in which a single projection 22 is provided, and FIG. 3B shows a case in which two projections 22 are provided in parallel relation.

Referring to FIGS. 2, 3A and 3B, the structure of the gasket 13 according to this embodiment will be described in greater detail.

The gasket 13 includes the main body 14, and the inert resin film 15 provided on the surface of the main body 14. The main body 14 is merely required to be made of the elastic material, which is not particularly limited. Examples of the elastic material include thermosetting rubbers and thermoplastic elastomers. Of these elastic materials, the thermosetting rubbers and dynamically crosslinkable thermoplastic elastomers having crosslinking sites are more preferred because of their excellent heat resistance. These polymer components for the elastic material are not particularly limited, but preferred examples include ethylene-propylene-diene rubbers and butadiene rubbers which are excellent in moldability. Other preferred examples include butyl rubbers, chlorinated butyl rubbers and brominated butyl rubbers which are excellent in gas barrier property. That is, all kinds of synthetic rubbers and thermoplastic elastomers, and blends of any of these synthetic rubbers and thermoplastic elastomers are usable as the material for the main body 14. Specific examples include butyl rubbers, halogenated butyl rubbers, styrene butadiene rubbers, butadiene rubbers, epichlorohydrin rubbers, neoprene rubbers and ethylene propylene rubbers.

The type of the inert resin film 15 to be provided on the surface of the main body 14 is not particularly limited, as long as the inert resin film is capable of preventing migration of substances from the crosslinked rubber (main body 14) and has more excellent slidability, i.e., a smaller friction coefficient, than the rubber. Examples of the inert resin film include films of ultrahigh-molecular-weight polyethylenes and fluororesins which are proved to be practical in medical applications. The fluororesin films are particularly preferred because they are excellent in slidability and have chemically stable surfaces. Usable examples of the fluororesins include conventionally known fluorine-containing resins such as polytetrafluoroethylene (PTFE), modified PTFE, ethylene tetrafluoroethylene copolymers (ETFE) and perfluoroalkyl ether (PFA). The ultrahigh-molecular-weight polyethylenes (UHMWPE) may be used. The PTFE and the modified PTFE are preferred because of their excellent slidability and chemical stability. The ETFE is also preferred because of its higher resistance toy-ray sterilization. For adhesion to the main body 14, a film made of a mixture of these resins or a laminate film of these resins may be used.

An inner surface of the inert resin film to be provided on the main body 14 (to be brought into contact with the main body 14) is preferably processed for adhesion. The method for the adhesion processing is not particularly limited. A preferred example of the adhesion processing is ion beam processing which is unlikely to chemically alter the film and obviates the use of an adhesive agent.

The laminated gasket 13 according to this embodiment has the circumferential surface portion 17 to be kept in gas-tight and liquid-tight contact with the inner surface 16 of the syringe barrel 11, and the annular projection 22 is provided on the inert resin film 15 on the circumferential surface portion 17 as extending circumferentially of the circumferential surface portion 17.

The projection 22 is annular and extends along the entire circumference of the circumferential surface portion 17. In an embodiment shown in FIGS. 3A and 4A, a single projection 22 is provided by way of example. In an embodiment shown in FIGS. 3B and 4B, two projections 22 are provided by way of example.

It is merely necessary to provide at least one projection 22, but a plurality of projections may be provided so as to be spaced a predetermined distance from each other axially of the gasket 13. Thus, the number of the projections 22 is not particularly limited.

With the circumferential surface portion 17 of the gasket 13 being seen in a development elevation, the projection 22 preferably extends generally linearly without local directionality.

FIGS. 4A and 4B are enlarged sectional views each showing a contact portion between the circumferential surface portion of the gasket and the inner surface of the syringe barrel of the medical syringe according to the embodiment of the present invention. FIG. 4A shows the case in which the single projection 22 is provided, and FIG. 4B shows the case in which the two parallel projections 22 are provided.

When the gasket 13 is inserted into the syringe barrel 11, the projection 22 provided on the circumferential surface portion 17 of the gasket 13 is pressed against the inner surface 16 of the syringe barrel 11, and non-contact surface portions 23 are defined along widthwise opposite edges of the projection 22 with respect to the inner surface 16 of the syringe barrel 11. Thus, only the projection 22 is kept in contact with the inner surface 16 of the syringe barrel 11 around the projection 22, so that a contact pressure between the gasket 13 and the syringe barrel 11 is locally increased to improve the sealability. Since the contact pressure is locally increased, it is possible to suppress the increase in sliding resistance.

The effect of the present invention can be provided by first molding the gasket 13 and then forming the projection 22. If the molding of the gasket 13 and the formation of the projection 22 are achieved simultaneously, i.e., if a mold preliminarily formed with a structure corresponding to the projection is used for the molding and the projection structure is transferred to the gasket, the projection structure formed by the molding is liable to be scratched or damaged during demolding of the resulting gasket. Further, scratches and the like occurring during the molding and the demolding of the gasket can be repaired to some extent by forming the projection 22 in the projection forming step subsequent to the molding step.

An exemplary method for the formation of the projections 22 is to apply heat to a surface layer of the laminated gasket 13 as abase to evaporate or decompose a surface portion of the inert resin film 15 and redeposit a part of the evaporated material to form the projections 22 (see FIGS. 3B and 4B).

An exemplary method for applying the heat is to apply a laser beam. The processing by the application of the laser beam is advantageous because it can form a minute projection structure and is less liable to influence the periphery of the projection formation area.

A known technique may be used for determination of the type and the output of the laser beam for the laser beam processing. The type of the laser beam may be properly selected according to the material for the film, the height of the projections 22 and the like. A processing method using an infrared laser beam is preferred for industrial handling ease. A laser beam application period may be properly selected according to conditions for the formation of the projections. Particularly, application of a short-pulse laser beam is preferred because the periphery of the projection formation area is less liable to be thermally influenced.

Another exemplary method for the formation of the projections 22 is to grind or cut the surface of the lamination film 15 to partly compress the material (the material of the surface portion of the lamination film 15) (to form so-called burrs) by the stress to form the projections 22.

Further another exemplary method for the formation of the projection 22 is to form the projection 22 from a fluid material such as an emulsion containing a fluororesin (e.g., PTFE) by a spraying method or the like and solidify the fluid material projection thus formed by heating or cooling (see FIGS. 3A and 4A).

A contact surface portion of the projection 22 to be kept in contact with the inner surface 16 of the syringe barrel 11 preferably has a width W of not greater than 50 μm, more preferably not greater than 40 μm. In the present invention, only the projection 22 is kept in contact with the inner surface 16 of the syringe barrel 11 around the projection 22, whereby the contact pressure between the gasket 13 and the syringe barrel 11 is increased. In order to increase the contact pressure, it is preferred to minimize the width W of the contact surface portion of the projection 22 in contact with the inner surface 16 of the syringe barrel 11. If the width W of the contact surface portion of the projection 22 in contact with the inner surface 16 of the syringe barrel 11 is greater than the aforementioned range, the contact sliding resistance is liable to increase.

The non-contact surface portions 23 defined along the widthwise opposite edges of the projection 22 with respect to the inner surface 16 of the syringe barrel 11 preferably each have a width A of not less than 25 μm, more preferably not less than 30 μm. In order to increase the contact pressure of the contact surface portion of the projection 22 with respect to the inner surface 16 of the syringe barrel 11, it is advantageous to maximize the widths A of the non-contact surface portions 23 with respect to the inner surface 16 of the syringe barrel 11.

Next, a method for producing the gasket 13 according to this embodiment will be described.

The gasket 13 according to this embodiment is produced through the following production process steps:
(1) preparing a gasket molding mold;
(2) molding a gasket laminated with an inert resin film in the mold; and
(3) removing the laminated gasket from the mold, and then forming an annular projection on a circumferential surface portion of the gasket circumferentially of the circumferential surface portion.

In the step of molding the gasket laminated with the inert resin film in the mold, an unvulcanized rubber is put on an inner surface of the inert resin film in the mold, and vulcanization-molded.

For example, a sheet of an unvulcanized rubber containing a crosslinking agent is stacked on the inert resin film, and vulcanization-molded in the mold. Thus, the gasket is produced as having a predetermined shape.

In this case, the inner surface of the inert resin film 15 on which the rubber is to be put is preferably preliminarily roughened. With the inner surface of the inert resin film 15 roughened, the rubber can firmly adhere to the inert resin film 15 by the vulcanization molding without the use of an adhesive agent or the like. The adhesion is attributable to an anchoring effect which is created with the vulcanized rubber intruding into voids formed in the roughened inner surface of the inert resin film 15.

The modification of the inner surface of the inert resin film 15 may be achieved, for example, by applying an ion beam to the inner surface to break the internal molecular structure in the inner surface for the roughening (see, for example, JP4908617B).

The gasket can be produced as having excellent sealability by molding the gasket in the mold and then forming the projection 22.

The method for forming the projection after the molding of the gasket is as previously described.

Examples

[Production of Gasket]

The adhesion processing was performed on one surface of an inert resin film (skived PTFE film VALFLON available from Nippon Valqua Industries, Ltd. and having a film thickness of 70 μm and a center line average surface roughness of 0.11 μm), and an unvulcanized rubber sheet of chlorinated butyl rubber (having a JIS A hardness of 58 degrees) was stacked on the surface of the inert resin film on a molding mold. The resulting stack was vulcanization-molded into gasket structures at 175° C. for 6 minutes by a vacuum press.

was measured by means of a precision universal tester (AG-X 50 kN available from Shimadzu Corporation). An average force required for sliding the gasket for a sliding distance of 10 mm to 15 mm was determined as the sliding resistance.

Liquid Drug Sealability

The test samples were each filled with a test liquid, and then an opposite end of the syringe barrel was capped. The test samples were allowed to stand still at 40° C. for 2 months, and then observed with an objective lens having a magnification of 50× by means of a video microscope (DVM5000 available from Leica Microsystems Inc.) to be checked for liquid leakage. For each of the test samples, 10 products were observed, and the number of products suffering from liquid leakage (in which the test liquid penetrated beyond a maximum diameter portion of the gasket) was recorded. A test sample with two or less products suffering from the liquid leakage was rated as acceptable. The test liquid herein used was prepared by adding 0.2 g/L of a colorant (red food colorant available from Tokyo Chemical Industry Co., Ltd.) and 1.0 g/L of a surfactant (POLYSORBATE 80 available from NOF Corporation) to water.

TABLE 1

|  | Example 1 | Example 2 | Example 3 | Comparative Example 1 | Comparative Example 2 | Comparative Example 3 |
| --- | --- | --- | --- | --- | --- | --- |
| Maximum width (μm) of contact surface portion | 30 | 32 | 35 | 25 | 55 | — |
| Minimum width (μm) of non-contact surface portions | 45 | 60 | 33 | 25 | 40 | — |
| Sliding resistance (N) | 8.43 | 8.14 | 8.34 | 8.27 | 8.65 | 8.43 |
| Liquid drug sealability (number) | 0/10 | 0/10 | 0/10 | 4/10 | 4/10 | 6/10 |

Then, gaskets (Examples 1 to 3 and Comparative Examples 1 and 2) were each produced by forming an annular projection extending circumferentially on the circumferential surface portion of the gasket structure. A gasket (Comparative Example 3) was produced without forming the annular projection.

[Formation of Projection]

The formation of the projection was achieved through the laser beam processing by applying a laser beam at a wavelength of 9300 nm by means of 3-Axis CO2 Laser Marker ML-Z9550T available from Keyence Corporation.

[Production of Syringe Barrel]

The gaskets thus produced were each inserted into a 1-mL COP resin syringe barrel (having a barrel inner diameter of 6.35 mm), whereby test samples were produced.

[Test Method]

Measurement of Dimensions of Contact Surface Portion and Non-Contact Surface Portions For each of the test samples, a contact surface portion (black image portion) and non-contact surface portions (white image portions) of the circumferential surface portion of the gasket with respect to the inner surface of the syringe barrel were observed in ten given parts for measurement of the widths thereof, and a maximum width and a minimum width of the contact surface portion and the non-contact surface portions were determined.

Measurement of Sliding Resistance

A plunger was attached to the gasket of each of the test samples, and a force required for squeezing the gasket at a speed of 100 mm/minute in the syringe barrel by the plunger

[Test Results]

The test sample of Comparative Example 2 suffered from the liquid leakage, because the contact surface portion had a greater width and hence a reduced contact pressure.

The test samples of Examples 1 to 3 were excellent with significantly reduced numbers of products suffering from the liquid leakage as compared with the test sample of Comparative Example 3 in which the projection was not formed after the molding of the gasket, the test sample of Comparative Example 1 in which the non-contact surface portions kept out of contact with the inner surface of the syringe barrel each had a smaller width, and the test sample of Comparative Example 2 in which the projection had a greater contact width. In the test samples of Examples 1 to 3, the sliding resistance was lower than in the test sample of Comparative Example 3 in which the projection was not formed after the molding of the gasket.

This application corresponds to Japanese Patent Application No. 2016-255269 filed in the Japan Patent Office on Dec. 28, 2016, the disclosure of which is incorporated herein by reference in its entirety.

What is claimed is:

1. A syringe comprising:
   a hollow cylindrical syringe barrel; and
   a gasket fitted in the syringe barrel;
   wherein the gasket includes a main body made of an elastic material, and an inert resin film provided on a surface of the main body;
   wherein the gasket has a circumferential surface portion which is made by the inert resin film substantially kept in contact with an inner surface of the syringe barrel, and an annular projection provided on the inert resin film on the circumferential surface portion as extending circumferentially of the circumferential surface portion;

wherein the projection has a contact surface portion kept in contact with the inner surface of the syringe barrel and having a width of not less than 30 μm and not greater than 40 μm;

wherein the circumferential surface portion has non-contact surface portions located out of contact with the inner surface of the syringe barrel on widthwise opposite sides of the projection and having a width of not less than 30 μm.

2. The syringe according to claim 1, wherein the inert resin film comprises at least one of a polytetrafluoroethylene, an ethylene-tetrafluoroethylene copolymer and an ultra-high-molecular-weight polyethylene, and a mixture of any of these polymers.

3. The syringe according to claim 2, which is a prefilled syringe in which the syringe barrel is prefilled with a liquid drug.

4. The syringe according to claim 1, which is a prefilled syringe in which the syringe barrel is prefilled with a liquid drug.

* * * * *